(12) United States Patent
Nguyen et al.

(10) Patent No.: US 11,067,501 B2
(45) Date of Patent: Jul. 20, 2021

(54) FABRIC VALIDATION USING SPECTRAL MEASUREMENT

(71) Applicant: Inspectorio Inc., Minneapolis, MN (US)

(72) Inventors: Binh Thanh Nguyen, Ho Chi Minh (VN); Han Ky Cao, Ho Chi Minh (VN); Cuong Van Nguyen, Ho Chi Minh (VN); Carlos Moncayo, Minneapolis, MN (US)

(73) Assignee: Inspectorio, Inc., Minneapolis, MN (US)

( * ) Notice: Subject to any disclaimer, the term of this patent is extended or adjusted under 35 U.S.C. 154(b) by 0 days.

(21) Appl. No.: 16/596,997

(22) Filed: Oct. 9, 2019

(65) Prior Publication Data

US 2020/0309689 A1    Oct. 1, 2020

(30) Foreign Application Priority Data

Mar. 29, 2019  (VN) .............................. 1-2019-01597

(51) Int. Cl.
*G01N 21/3563* (2014.01)
*G01J 3/02* (2006.01)
(Continued)

(52) U.S. Cl.
CPC ........ *G01N 21/3563* (2013.01); *G01J 3/0272* (2013.01); *G01J 3/0291* (2013.01);
(Continued)

(58) Field of Classification Search
CPC . G06T 2207/30124; B07C 5/34; B07C 5/342; B07C 5/3422; B07C 5/344; G06F 16/53; G06F 16/535; G06F 16/538; G06F 16/56; G06F 16/58; G06F 16/583; G06F 16/5838; G06F 16/5862; G06K 9/00536;
(Continued)

(56) References Cited

U.S. PATENT DOCUMENTS 6,272,479 B1 *   8/2001   Farry .................. G06K 9/6217
                                                        706/13
7,071,469 B2 *   7/2006   Berghmans ........ G01N 21/8915
                                                       250/339.01

(Continued)

FOREIGN PATENT DOCUMENTS

WO   WO-2020109170 A1 *   6/2020   ........... G01N 33/367

OTHER PUBLICATIONS

Cao, Jing et al., "Near-Infrared Spectroscopy for Anticounterfeiting Innovative Fibers," 2013, Hindawi Publishing Corporation, ISRN Textiles, vol. 2013, Article ID 649407, 4 pages. (Year: 2013).*
(Continued)

*Primary Examiner* — Gordon J Stock, Jr.
(74) *Attorney, Agent, or Firm* — Polsinelli, P.C.

(57) ABSTRACT

Fabric validation using spectral measurement is provided. In various embodiments, a near-infrared absorption spectrum of a fabric sample is received from a near-infrared spectrometer. A plurality of features is extracted from the spectrum. The plurality of features is provided to a trained classifier. The trained classifier provides a similarity score indicative of the similarity of the fabric sample to a reference fabric sample.

36 Claims, 8 Drawing Sheets

(51) Int. Cl.
| | |
|---|---|
| *G01N 21/359* | (2014.01) |
| *G01N 33/36* | (2006.01) |
| *G01J 3/28* | (2006.01) |
| *G06K 9/00* | (2006.01) |
| *G06N 3/08* | (2006.01) |
| *G01J 3/46* | (2006.01) |

(52) U.S. Cl.
CPC .............. *G01J 3/28* (2013.01); *G01N 21/359* (2013.01); *G01N 33/367* (2013.01); *G06K 9/00536* (2013.01); *G06N 3/08* (2013.01); *G01J 3/0297* (2013.01); *G01J 3/462* (2013.01); *G01N 2201/129* (2013.01); *G01N 2201/1296* (2013.01)

(58) Field of Classification Search
CPC .. G06K 9/6256; G06K 9/6267; G06K 9/6269; G06K 9/00; G06K 9/4628; G06K 9/6217; G06K 9/627; G16C 20/70; G06N 20/10; G06N 20/00; G06N 3/08; G06N 3/0454; G01J 3/0297; G01J 3/462; G01J 3/42; G01J 3/0291; G01J 3/0272; G01J 3/28; G01J 2003/2826; G01N 2201/1293; G01N 2201/129; G01N 33/367; G01N 21/25; G01N 21/3563; G01N 21/359; G01N 2201/1296
See application file for complete search history.

(56) References Cited

U.S. PATENT DOCUMENTS

| | | | | |
|---|---|---|---|---|
| 7,617,163 | B2* | 11/2009 | Ben-Hur | G06K 9/6215 706/12 |
| 8,081,304 | B2* | 12/2011 | Furness, III | G01J 3/0264 356/71 |
| 8,452,716 | B2* | 5/2013 | Howley | G01J 3/28 706/12 |
| 10,307,795 | B2* | 6/2019 | Dominguez Holguin | B07C 5/34 |
| 10,936,921 | B2* | 3/2021 | Gesley | G06K 9/00134 |
| 2004/0119972 | A1* | 6/2004 | Smit-Kingma | G01N 21/95 356/238.1 |
| 2010/0036795 | A1* | 2/2010 | Busch | G01N 21/3563 706/54 |
| 2010/0290032 | A1* | 11/2010 | Bugge | B07C 5/342 356/51 |
| 2017/0032285 | A1* | 2/2017 | Sharma | G06N 3/0454 |
| 2020/0042822 | A1* | 2/2020 | Chae | G01N 21/3581 |
| 2020/0249085 | A1* | 8/2020 | Neumaier | G01J 3/0264 |
| 2020/0320769 | A1* | 10/2020 | Chen | G06K 9/6256 |

OTHER PUBLICATIONS

Davis, Christopher et al., "Rapid, Non-Destructive, Textile Classification Using SIMCA on Diffuse Near-Infrared Reflectance Spectra ," 2015, Journal of Modern Physics, 6, pp. 711-718. (Year: 2015).*

Fan, Kuo-Chin et al., "Fabric Classification Based on Recognition Using a Neural Network and Dimensionality Reduction," 1998, Textile Research Journal 68(3), pp. 179-185. (Year: 1998).*

Jasper, Warren J. et al., "Using Neural Networks and NIR Spectrophotometry to Identify Fibers," 1994, Textile Research Journal 64(8), pp. 444-448. (Year: 1994).*

Jin, Xiaoke et al., "Spectral characterization and discrimination of synthetic fibers with near-infrared hyperspectral imaging system," 2017, Applied Optics, vol. 56, No. 12, pp. 3570-3576 (Year: 2017).*

Langeron, Y. et al., "Classifying NIR spectra of textile products with kernel methods," 2007, Engineering Applications of Artificial Intelligence 20, pp. 415-427. (Year: 2007).*

Nayak, Rajkishore et al., Chapter 5: 'Artificial intelligence and its application in the apparel industry' of Automation in Garment Manufacturing, 2018, pp. 109-138. (Year: 2018).*

Sun, Xudong et al., "Classification of textile fabrics by use of spectroscopy-based pattern recognition methods," 2016, Spectroscopy Letters, vol. 49, No. 2, pp. 96-102. (Year: 2016).*

Tan, Chao et al., "Category identification of textile fibers based on near-infrared spectroscopy combined with data description algorithms," 2019 (available online Nov. 17, 2018), Vibrational Spectroscopy 100, pp. 71-78. (Year: 2018).*

* cited by examiner

FABRIC VALIDATION USING SPECTRAL MEASUREMENT

CROSS-REFERENCE TO RELATED APPLICATIONS

This application claims the benefit under 35 USC 119(a) of Vietnamese Patent Application No. 1-2019-01597, filed on Mar. 29, 2019, which is hereby incorporated by reference in its entirety.

BACKGROUND

Embodiments of the present disclosure relate to fabric validation, and more specifically, to fabric validation using spectral measurement.

BRIEF SUMMARY

According to embodiments of the present disclosure, methods of and computer program products for fabric validation are provided. In various embodiments, a near-infrared absorption spectrum of a fabric sample is received from a near-infrared spectrometer. A plurality of features is extracted from the spectrum. The plurality of features is provided to a trained classifier. The trained classifier provides a similarity score indicative of the similarity of the fabric sample to a reference fabric sample.

In various embodiments, the near-infrared spectrometer comprises a hand-held spectrometer. In various embodiments, providing the plurality of features to the trained classifier comprises sending the plurality of features to a remote fabric validation server, and obtaining from the trained classifier the similarity score comprises receiving the similarity score from the fabric validation server. In various embodiments, said sending and receiving is performed via a wide area network.

In various embodiments, extracting a plurality of features from the spectrum comprises noise reduction.

In various embodiments, wavelength, intensity, and/or reflectance are received from the near-infrared spectrometer, and extracting the plurality of features further comprises extracting features from the wavelength, intensity, and/or reflectance.

In various embodiments, the trained classifier comprises an artificial neural network. In various embodiments, extracting the plurality of features comprises principal component analysis. In various embodiments, extracting the plurality of features comprises applying an artificial neural network. In various embodiments, the artificial neural network comprises at least one convolutional layer. In various embodiments, the artificial neural network comprises a plurality of 1D convolutional layers.

In various embodiments, a fabric material composition, weave type, thread count, yarn thickness, and/or color is obtained from the trained classifier. In various embodiments, obtaining the similarity score comprises providing features extracted from a reference sample to the trained classifier. In various embodiments, the similarity score is provided to a user. In various embodiments, the fabric material composition, weave type, thread count, yarn thickness, and/or color are provided to a user.

DETAILED DESCRIPTION

Figure 1:
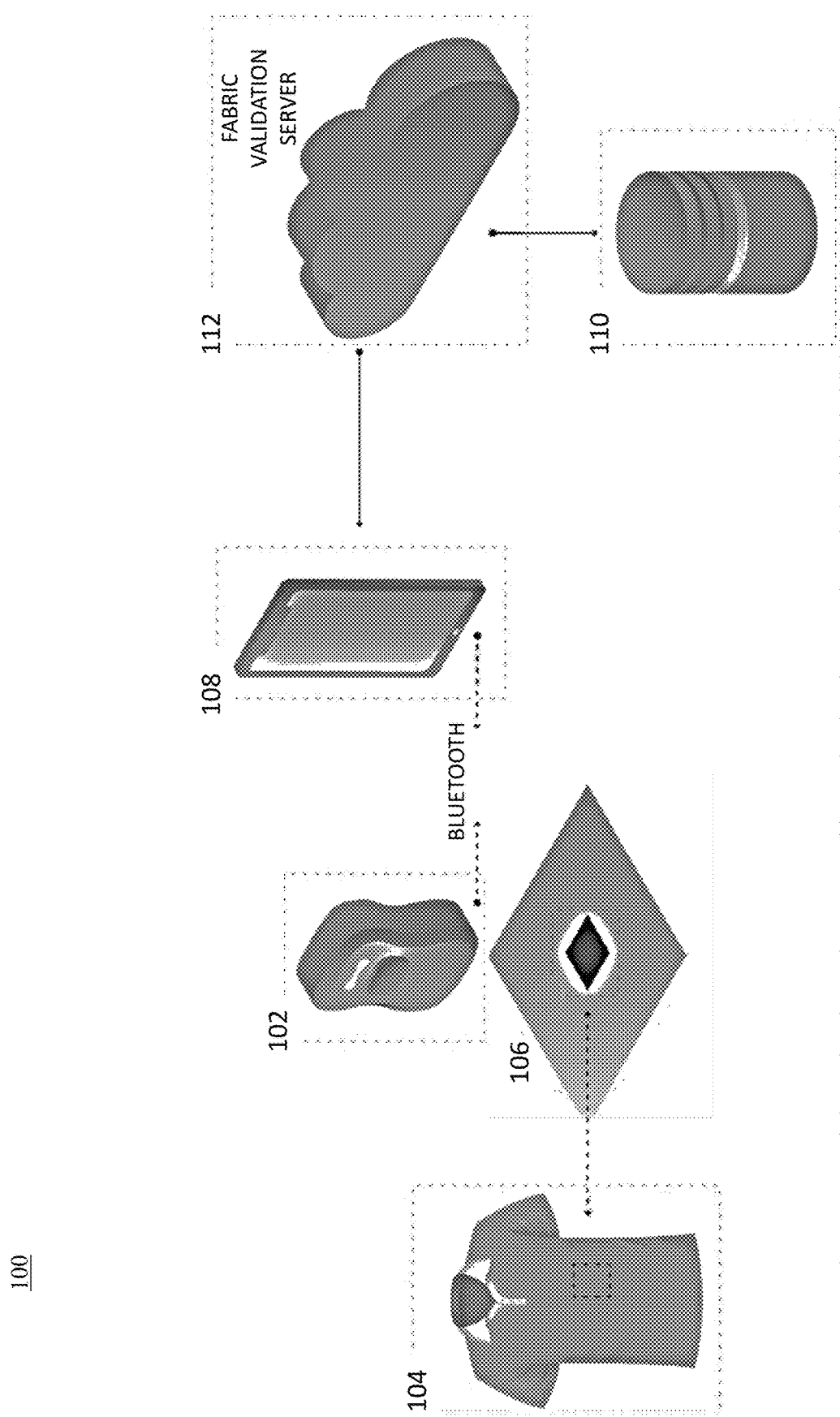
FIG. 1 is a schematic view of an exemplary system for fabric validation according to embodiments of the present disclosure.

Fabric validation is an important step in textile and apparel inspection. During fabric validation, all materials used in the production of an article are matched to the requested ones to verify correctness. Fabric validation generally occurs during textile production. In a manual inspection process, auditors go to a given factory to carefully examine production items to ensure product quality before delivery to distributors. Current validation processes are generally performed by experienced inspectors or certified laboratories, which are costly and time-consuming.

To address these and other shortcomings of alternative methods, the present disclosure provides a framework for verification that a set of textile samples are made from a given reference fabric by using spectral measurement devices.

For each reference fabric, its NIR (Near Infrared Spectroscopy) spectrum is collected and stored. As set out in further detail below, an efficient machine-learning method may then be applied to constantly compute the matching probability between a given sample and the spectrum data of a reference fabric. Because spectral signals may be sensitive to environmental noise and the particular methods used to collect the spectral signal data, machine learning methods may be used to match a sample to a reference fabric even if the spectrum of the sample does not perfectly match the reference spectrum. Even when samples are taken from the same fabric, the corresponding spectral values (e.g., absorbance or reflectance) may have an observable variation. In various embodiments, machine-learning may be used for extracting important patterns from spectral data and then computing the spectrum similarity between two fabrics (e.g., a reference fabric and a sample).

Based on the matching probability, various actions may be taken. For example, where the matching probability exceeds a predetermined threshold (e.g., 70%, 80%, 90%), an indication may be provided to a user that the fabric is as expected. Where the matching probability is below the predetermined threshold, an indication may be provided to the user that the fabric is not as expected. A remedial or reporting action may be suggested to the user in such cases. Auditors can notify the corresponding brands or retailers about the matching results and then they can choose appropriate actions (for example, pass/fail the current inspection or suggest for doing another re-inspection).

The approaches described herein significantly reduce the cost of the validation process and minimize the risk of inspection failures.

In various embodiments, a framework is provided for fabric validation by comparing a textile sample with a reference fabric to ensure that the sample is has the expected characteristics.

In various embodiments, an inspector extracts a textile sample from inspected items and uses a spectral measurement device to collect the corresponding NIR spectrum of the sample. In various embodiments, the spectral data are provided by the measurement device to a local computing device (e.g., mobile phones or personal computers). In some embodiments, the measurement device is integrated with the computing device. In some embodiments, the measurement device communicates with the computing device wirelessly, e.g., via Bluetooth. In some embodiments, the measurement device communicates with the computing device via a wired connection.

In some embodiments, the local computing device communicates with a remote fabric validation server for validation of the data. As set out further below, the fabric validation server may include a learning system that is configured to validate the data as belonging to a given fabric. In some embodiments, the server provides the results of validation back to the local computing device, which in turn displays the validation results to a user.

In some embodiments, a feature vector is provided to a learning system. Based on the input features, the learning system generates one or more outputs. In some embodiments, the output of the learning system is a feature vector.

In some embodiments, the learning system comprises a SVM. In other embodiments, the learning system comprises an artificial neural network. In some embodiments, the learning system is pre-trained using training data. In some embodiments training data is retrospective data. In some embodiments, the retrospective data is stored in a data store. In some embodiments, the learning system may be additionally trained through manual curation of previously generated outputs.

In some embodiments, the learning system, is a trained classifier. In some embodiments, the trained classifier is a random decision forest. However, it will be appreciated that a variety of other classifiers are suitable for use according to the present disclosure, including linear classifiers, support vector machines (SVM), or neural networks such as recurrent neural networks (RNN).

Suitable artificial neural networks include but are not limited to a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network.

Referring now to FIG. 1, an exemplary system for fabric validation is illustrated according to embodiments of the present disclosure. System 100 includes spectral measurement device 102, local computing device 108, validation server 112, and datastore 110.

In some embodiments, spectral measurement device 102 comprises a hand-held spectrometer. In some embodiments, the handheld spectrometer comprises a device such as the DLP NIRscan Nano Module from Texas Instrument (http://www.ti.com/tool/DLPNIRNANOEVM). It is noted that the terms spectrometer and spectroscope are generally used interchangeably in the art.

In some embodiments, local computing device 108 comprises a tablet, smartphone, PDA, laptop, or personal computer. In some embodiments, local computing device 108 and spectral measurement device 102 are integrated. In some embodiments, local computing device 108 and spectral measurement device 102 are connected via a wired or wireless network. In some embodiments, the wireless network is a personal area network (PAN), such as Bluetooth.

In some embodiments, local computing device 108 communicates with server 112 via a wired or wireless network. In some embodiments, the connection between local computing device 108 and server 112 is provided via cellular data or WiFi.

An auditor examines an inspected item, such as T-shirt 104. A textile sample 106 is extracted. In some embodiments, the sample is extracted using measurement device 102. Measurement device 102 gathers a spectral data of the sample 104. As described above, the spectral data may be collected in the near-infrared (NIR).

The spectral data from spectral measurement device 102 is provided to local computing device 108 (which in some embodiment may be a mobile phone). In various embodiments, the spectral data may include a variety of information including, but not limited to, humidity, temperature, shift vector coefficients, exposure, PGA gain, wavelength, absorbance, reflectance, reference signals, and/or sample signals. In various embodiments, the local computing device may receive the spectral data (e.g., wavelength, absorbance, and/or reflectance) of both the sample fabric and the reference fabric. In various embodiments, the local computing device may apply one or more filters to the data to, e.g., filter out any environmental noise. In various embodiments, the original spectral data (e.g., wavelength, absorbance, and/or reflectance) in addition to first-order and second-order derivatives of these spectral signals may be provided to the local computing device from the spectral measurement device. The local computing device processes the spectrum, and then sent to fabric validation server 112. In some embodiments, validation server 112 is configured to apply a learning system to the input spectral data in order to determine the fabric type. In some embodiments, the learning system outputs a detected fabric type for display to the user. In some embodiments, the learning system outputs a probability of matching a selected reference fabric. In some embodiments, the learning system outputs probabilities of matching multiple reference fabrics.

In various embodiments, the validation server is configured to apply a learning system to the input spectral data in order to determine various features of a fabric. These features may include fabric material composition, weave type, thread count, yarn thickness, and/or color. In some embodiments, the learning system outputs the detected values for the plurality of features. In some embodiments, the learning system outputs probabilities of matching a selected reference fabric based on the features detected.

In various embodiments, a classifier includes a first component used to calculate two latent features from the spectral data of both the sample and the reference fabrics. In various embodiments, the input data is a one-dimensional (1D) vector computed from the spectral information. In various embodiments, the number of applicable features from the initial data may be reduced to improve computational performance and prevent overfitting. In various embodiments, a Principal Component Analysis (PCA) may be used for the input data. PCA is a dimension-reduction technique used in the feature engineering process to reduce a large number of variables (possibly correlated) into a smaller set of features containing important information in the initial data. For example, the input spectral data may include 288 points of absorbance values and the corresponding values of the first-order and the second-order derivatives of spectral signals so that it can have hundreds of dimensions. Reducing this dimension from the spectral information to a smaller value (e.g., 8 or 16) using PCA can enhance the performance of the classifier, especially when there are only a small number of samples in the one reference fabric.

In various embodiments, a deep neural network may be used for the feature extraction. In various embodiments, feature exaction may be implemented by applying an appropriate deep network to the 1D input data as is known in the art. For example, from the spectral input data, final features can be computed by going through multiple 1D convolutional neural networks with various window sizes (e.g., 3, 5, 7) combined with a max-pooling layer (e.g., with a window size of 2 and a stride of 3), and a number of fully-connected layers (e.g., 4 fully connected layers) with a latent vector whose size is exactly the desired size of the final feature vector (e.g., 4, 8 or 16). In various embodiments, the output of the feature extraction is a final fixed-size vector.

Figure 5A:
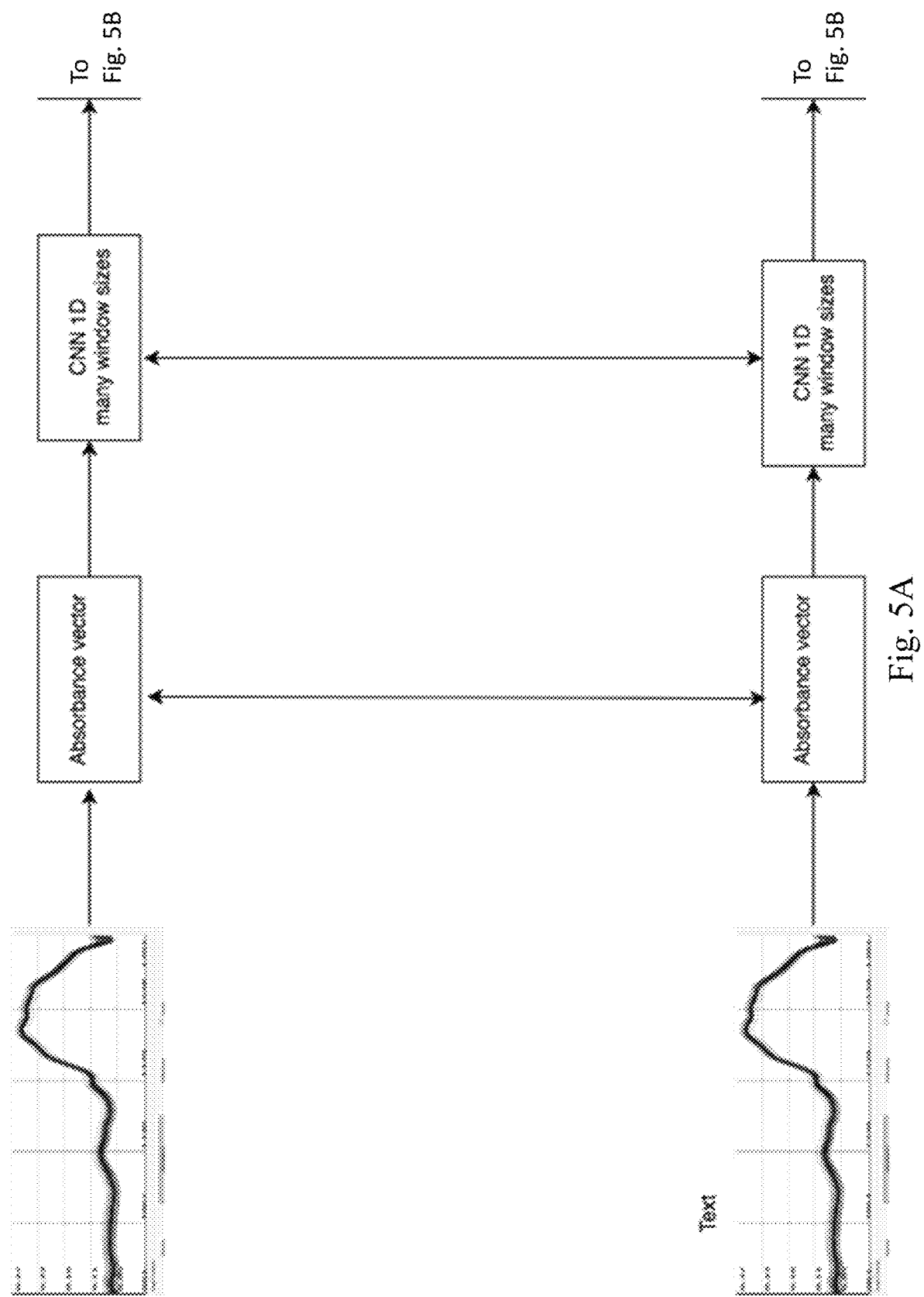
FIGS. 5A-5C illustrate a schematic diagram of a neural network according to embodiments of the present disclosure.
Figure 5B:
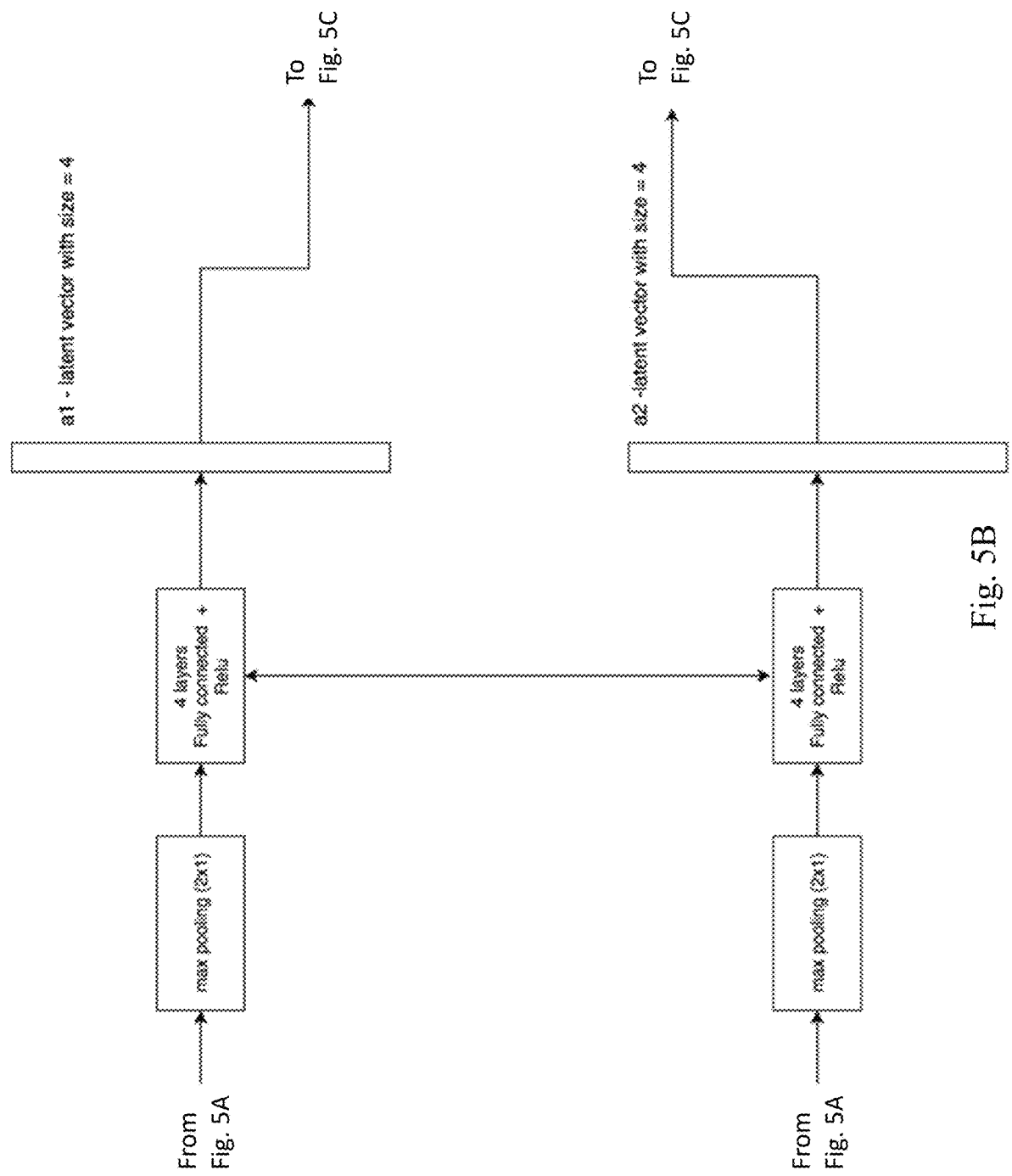
Figure 5C:
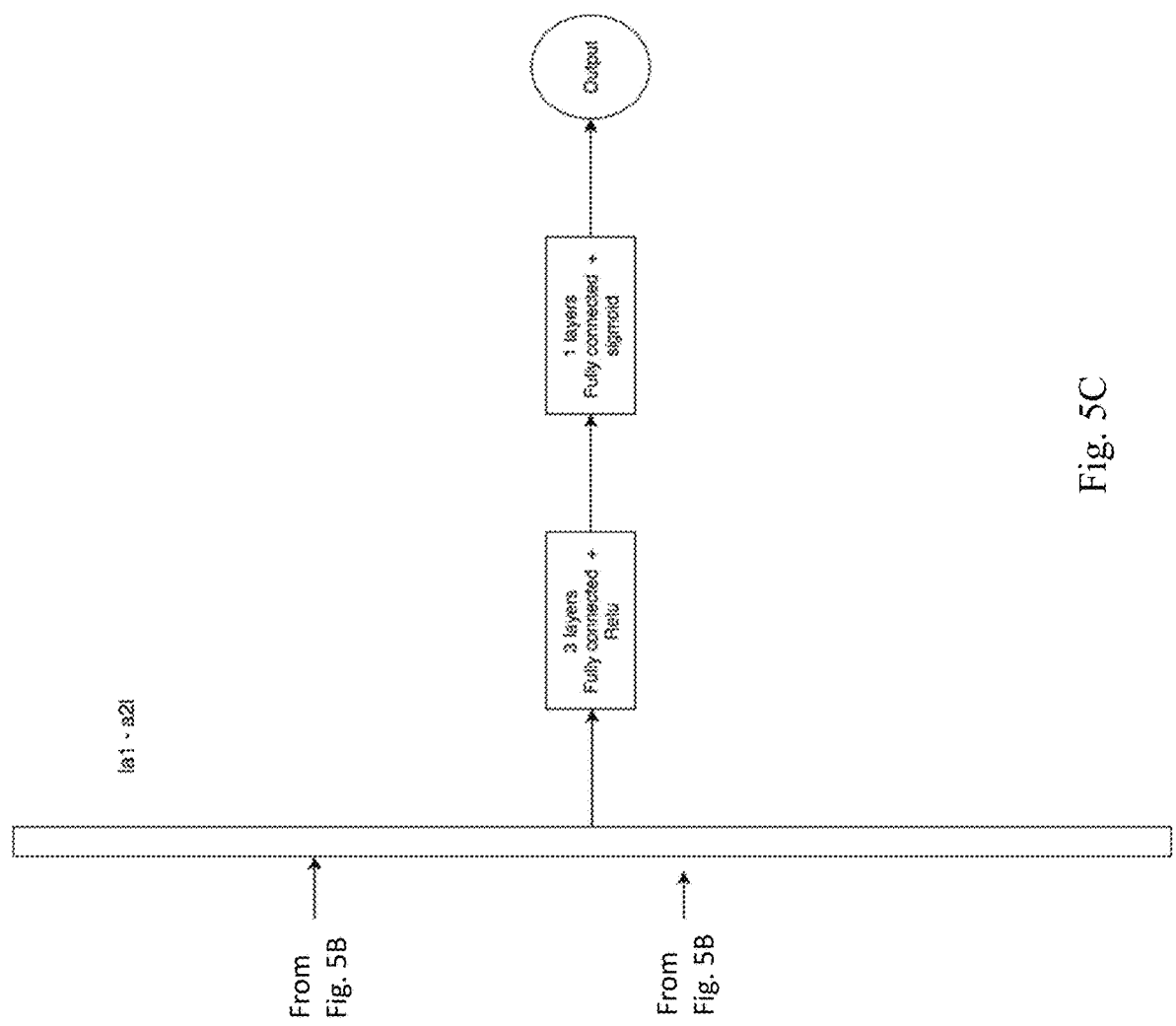

In various embodiments, the classifier includes a second component used to measure the similarity between two computed latent vectors to determine how similar these fabrics are under a threshold chosen by users. For the second component, there are multiple methods to measure the similarity between two vectors such as, e.g., the correlation, the cosine similarity, the Euclidean distance, Extreme Boosting Machine, Catboost, LightGBM, and deep neural networks. FIGS. 5A, 5B and 5C illustrate a schematic diagram of an exemplary neural network used for spectral similarity determination according to various embodiments of the present disclosure. For example, as shown in FIGS. 5A, 5B, and 5C, after the feature extraction step, the corresponding feature vectors from both reference and sample fabrics (a1 and a2) are extracted. A new vector, |a1-a2|, is determined by computing the absolute value of the difference of each coordinate between these two vectors. In various embodiments, the resulting new vector may pass through one or more (e.g., 3) fully connected layers using the Relu activation function. In various embodiments, the neural network may include a fully connected layer at the end to estimate the similarity of reference and sample fabrics. In various embodiments, after determining the similarity score, the final decision to conclude the sample fabric is similar to a given reference fabric or not depends on a threshold chosen. For example, if a threshold of 99% is selected, a sample fabric may be determined as being the same fabric as a reference fabric if the computed similarity score is greater than or equal to 99%.

Figure 2:
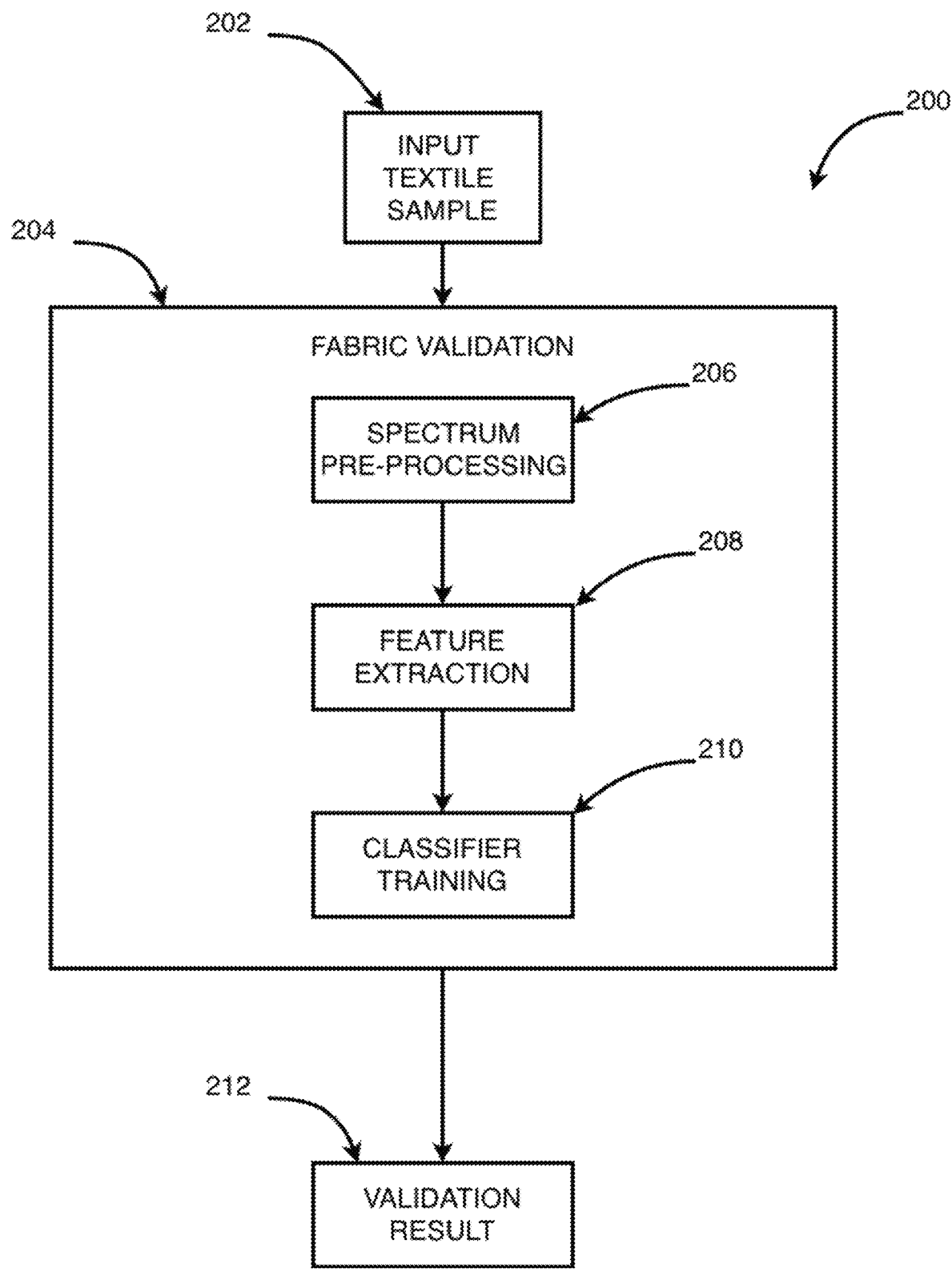
FIG. 2 illustrates a process for fabric validation according to embodiments of the present disclosure.

Referring now to FIG. 2, a process for fabric validation is illustrated according to embodiments of the present disclosure. Input textile sample 202 is provided for validation process 204, providing validation result 212. Fabric validation 204 employs a machine-learning model. The spectrum data extracted from spectrometers is preprocessed at 206 to reduce the influence of the environmental noises and the data collection process. Feature extraction 208 can use various signals collected from the spectral measurement device, including wavelength, intensity, absorbance, and reflectance. For example, wavelength and the corresponding absorbance or reflectance values may be used to perform the feature calculation. In some embodiments, PCA (Principal Component Analysis) is used. In some embodiments, a histogram of absorbance values among different intervals of wavelengths is used. In some embodiments, deep convolutional feature maps are used. In some embodiments, a combination of multiple types of features is used.

A classifier is trained at 210 to recognize each of a plurality of reference fabrics.

It will be appreciated that a variety of noise reduction methods may be applied as part of the preprocessing step. For example, smoothing, low-pass filtering, Principle Component Analysis (PCA) with or without reference channels, spline interpolation, and block averaging may be used for noise reduction in systems described herein.

Figure 3:
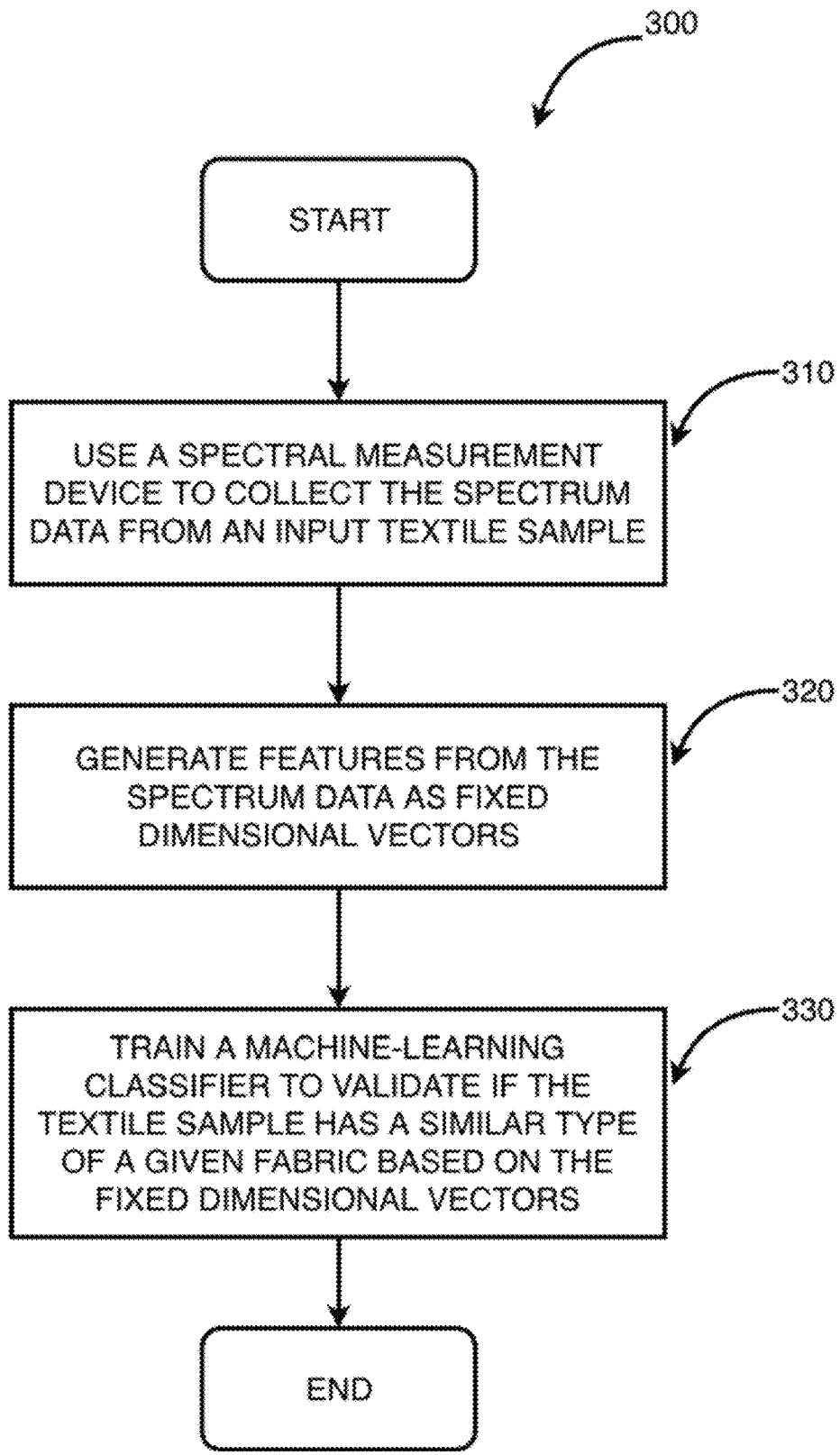
FIG. 3 illustrates a method for fabric validation is illustrated according to embodiments of the present disclosure.

Referring now to FIG. 3, a method for fabric validation is illustrated according to embodiments of the present disclosure. The computation steps of method 300 may be performed locally to an inspection site, may be performed by a remote server, e.g., a cloud server, or may be shared among a local computation device and a remote server. At 310, a spectral measurement device collects spectrum data from a textile sample. The input textile can consist of various objects that have different compositions, specifications, colors, warps, or wefts. At 320, a feature vector is generated from the spectrum data. As discussed above, these features may be computed using PCA or histogram computations. In some embodiments, multiple feature maps by one or more filters of a one-dimensional convolutional neural networks are used to extract fix-sized output vectors. At 330, using the fixed-size vectors computed at operation 320, a classifier is trained to validate if a textile sample has the same composition as a reference sample.

For each reference fabric, spectral data of a number of samples are collected. In some embodiments, they are stored in a datastore and then used for training. In some embodiments, a machine learning model (e.g., supervised-learning or unsupervised-learning) may be applied to the stored data. For a given test sample, features are extracted and provided to the trained classifier to measure the similarity of the spectrum of the testing sample with the training samples. In various embodiments, the output of the classifier is a similarity score corresponding to the similarity of the test sample to one or more of the reference fabrics. The similarity score may be compared to a predetermined threshold to determine a determination of a match or lack of match. The threshold may be chosen heuristically, or may be adaptively calculated during training. In various embodiments, the similarity score may be in the range [0,1]. In various embodiments, the threshold can adaptively be chosen for each reference dataset of a specific fabric such that the accuracy, the AUC, and the F1-score of the proposed machine-learning model can be maximized. In various embodiments, any sample with the similarity score greater than or equal to a selected threshold can be considered as "matching" the reference fabric.

Figure 4:
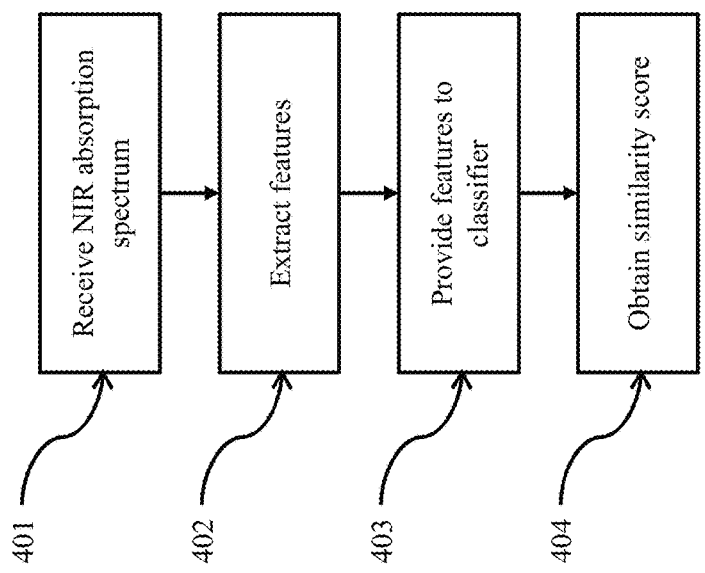
FIG. 4 illustrates a method for fabric validation according to embodiments of the present disclosure.

Referring now to FIG. 4, a method for fabric validation is illustrated. At 401, a near-infrared absorption spectrum of a fabric sample is received. At 402, a plurality of features is extracted from the spectrum. At 403, the plurality of features is provided to a trained classifier. At 404, the trained classifier provides a similarity score indicative of the similarity of the fabric sample to a reference fabric sample.

Figure 6:
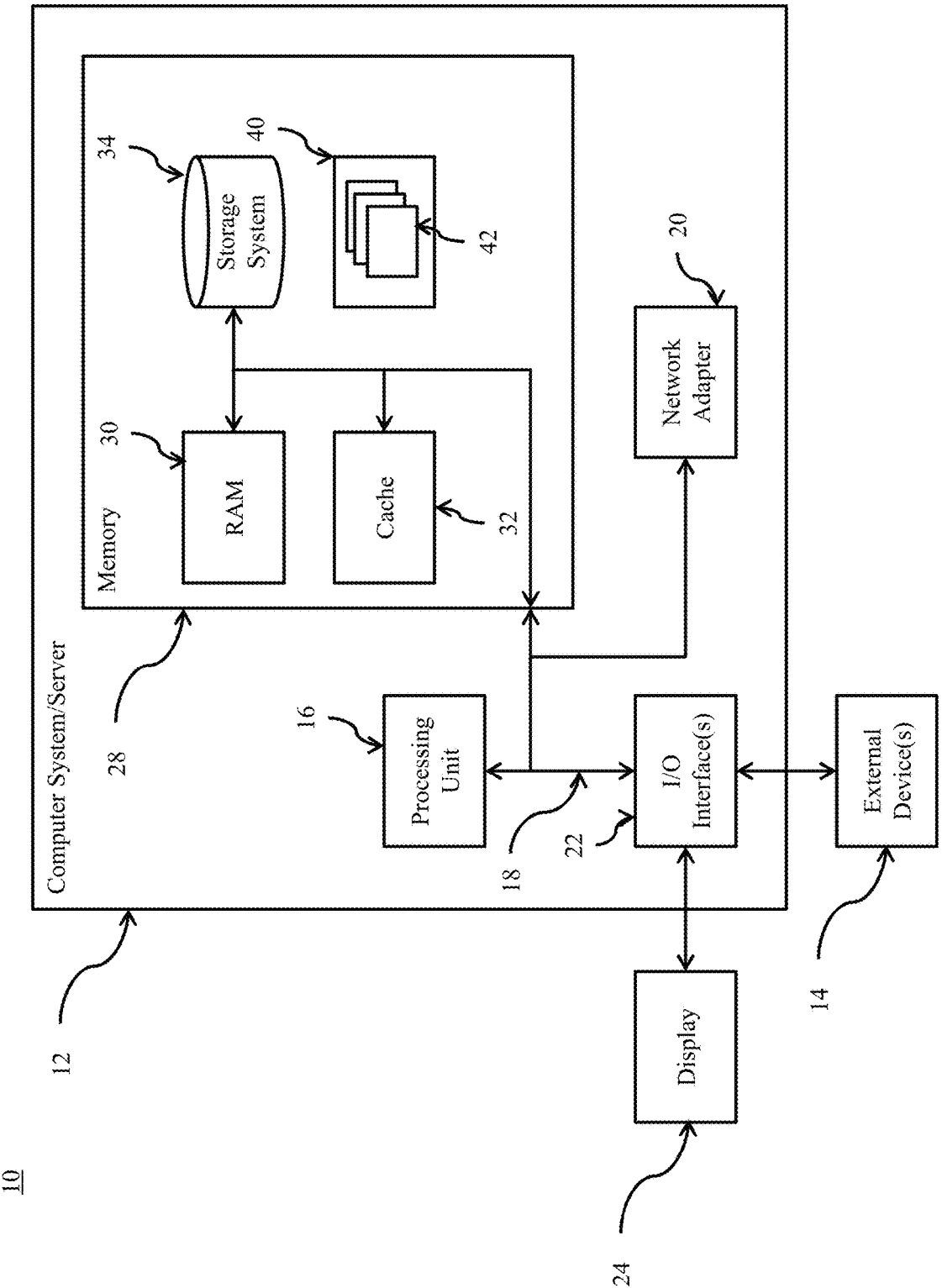
FIG. 6 depicts a computing node according to an embodiment of the present disclosure.

Referring now to FIG. 6, a schematic of an example of a computing node is shown. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present disclosure may be embodied as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system comprising:
a near-infrared spectrometer;
a computing node operatively coupled to the near-infrared spectrometer, the computing node comprising a computer readable storage medium having program instructions embodied therewith, the program instructions executable by a processor of the computing node to cause the processor to perform a method comprising:
receiving a near-infrared absorption spectrum of a fabric sample from the near-infrared spectrometer;
extracting a plurality of features from the spectrum;
generating at least one fixed-size vector from the plurality of features;
providing the at least one fixed-size vector to a trained classifier;
obtaining from the trained classifier a similarity score indicative of the similarity of the fabric sample to a reference fabric sample.

2. The system of claim 1, wherein the near-infrared spectrometer comprises a hand-held spectrometer.

3. The system of claim 1, wherein the computing node is local to the near-infrared spectrometer.

4. The system of claim 3, wherein the computing node and the near-infrared spectrometer are operatively coupled via a local area network.

5. The system of claim 4, wherein the local area network comprises a wireless network.

6. The system of claim 3, wherein the computing node and the near-infrared spectrometer are operatively coupled via a personal area network.

7. The system of claim 3, wherein the computing node and the near-infrared spectrometer are integrated into a handheld device.

8. The system of claim 1, wherein
providing the at least one fixed-size vector to the trained classifier comprises sending the at least one fixed-size vector to a remote fabric validation server, and
obtaining from the trained classifier the similarity score comprises receiving the similarity score from the fabric validation server.

9. The system of claim 8, wherein said sending and receiving is performed via a wide area network.

10. The system of claim 1, wherein extracting a plurality of features from the spectrum comprises noise reduction.

11. The system of claim 1, wherein the method further comprises:
receiving wavelength, intensity, and/or reflectance from the near-infrared spectrometer, and wherein extracting the plurality of features further comprises extracting features from the wavelength, intensity, and/or reflectance.

12. The system of claim 1, wherein the trained classifier comprises an artificial neural network.

13. The system of claim 1, wherein extracting the plurality of features comprises principal component analysis.

14. The system of claim 1, wherein extracting the plurality of features comprises applying an artificial neural network.

15. The system of claim 14, wherein the artificial neural network comprises at least one convolutional layer.

16. The system of claim 15, wherein the artificial neural network comprises a plurality of 1D convolutional layers.

17. The system of claim 1, wherein the method further comprises obtaining from the trained classifier a fabric material composition, weave type, thread count, yarn thickness, and/or color.

18. The system of claim 1, wherein obtaining the similarity score comprises providing at least one fixed-size vector extracted from a reference sample to the trained classifier.

19. The system of claim 1, the method further comprising providing the similarity score to a user.

20. The system of claim 17, further comprising providing the fabric material composition, weave type, thread count, yarn thickness, and/or color to a user.

21. A method comprising:
receiving a near-infrared absorption spectrum of a fabric sample from a near-infrared spectrometer;
extracting a plurality of features from the spectrum;
generating at least one fixed-size vector from the plurality of features;
providing the at least one fixed-size vector to a trained classifier;
obtaining from the trained classifier a similarity score indicative of the similarity of the fabric sample to a reference fabric sample.

22. The method of claim 21, wherein the near-infrared spectrometer comprises a hand-held spectrometer.

23. The method of claim 21, wherein
providing the at least one fixed-size vector to the trained classifier comprises sending the at least one fixed-size vector to a remote fabric validation server, and
obtaining from the trained classifier the similarity score comprises receiving the similarity score from the fabric validation server.

24. The method of claim 23, wherein said sending and receiving is performed via a wide area network.

25. The method of claim 21, wherein extracting a plurality of features from the spectrum comprises noise reduction.

26. The method of claim 21, further comprising:
receiving wavelength, intensity, and/or reflectance from the near-infrared spectrometer, and wherein extracting the plurality of features further comprises extracting features from the wavelength, intensity, and/or reflectance.

27. The method of claim 21, wherein the trained classifier comprises an artificial neural network.

28. The method of claim 21, wherein extracting the plurality of features comprises principal component analysis.

29. The method of claim 21, wherein extracting the plurality of features comprises applying an artificial neural network.

30. The method of claim 29, wherein the artificial neural network comprises at least one convolutional layer.

31. The method of claim 30, wherein the artificial neural network comprises a plurality of 1D convolutional layers.

32. The method of claim 21, further comprising obtaining from the trained classifier a fabric material composition, weave type, thread count, yarn thickness, and/or color.

33. The method of claim 21, wherein obtaining the similarity score comprises providing at least one fixed-size vector extracted from a reference sample to the trained classifier.

34. The method of claim 21, the method further comprising providing the similarity score to a user.

35. The method of claim 32, further comprising providing the fabric material composition, weave type, thread count, yarn thickness, and/or color to a user.

36. A computer program product for fabric validation, the computer program product comprising a computer readable storage medium having program instructions embodied therewith, the program instructions executable by a processor to cause the processor to perform a method comprising:
receiving a near-infrared absorption spectrum of a fabric sample from a near-infrared spectrometer;
extracting a plurality of features from the spectrum;
generating at least one fixed-size vector from the plurality of features;
providing the at least one fixed-size vector to a trained classifier;
obtaining from the trained classifier a similarity score indicative of the similarity of the fabric sample to a reference fabric sample.

* * * * *